United States Patent [19]

Tsunoda et al.

[11] Patent Number: 4,473,655

[45] Date of Patent: Sep. 25, 1984

[54] METHOD FOR THE RECOVERY OF RHODIUM COMPLEXES

[75] Inventors: Yoshitoshi Tsunoda, Tokyo; Taisei Tanimura; Chihiro Miyazawa, both of Okayama, all of Japan

[73] Assignee: Mitsubishi Chemical Industries, Limited, Tokyo, Japan

[21] Appl. No.: 340,917

[22] Filed: Jan. 20, 1982

[30] Foreign Application Priority Data

Jan. 22, 1981 [JP] Japan ................................ 56-8419

[51] Int. Cl.$^3$ ...................... B01J 31/40; B01J 31/24; C07C 45/50
[52] U.S. Cl. ............................. 502/24; 260/429 R; 502/30; 502/166; 568/454; 568/909
[58] Field of Search ............... 252/414, 411 R, 431 P; 260/429 R; 502/24, 30, 33, 53, 166

[56] References Cited

U.S. PATENT DOCUMENTS

| | | | |
|---|---|---|---|
| 3,560,539 | 2/1971 | Booth | 260/429 R |
| 3,965,192 | 6/1976 | Booth | 260/429 R |
| 4,131,640 | 12/1978 | Kutepow | 252/414 |
| 4,218,336 | 8/1980 | Eisenbach et al. | 252/414 |

FOREIGN PATENT DOCUMENTS 48-43799 12/1973 Japan .

*Primary Examiner*—P. E. Konopka
*Attorney, Agent, or Firm*—Sughrue, Mion, Zinn, Macpeak and Seas

[57] ABSTRACT

A method for the recovery of rhodium-triarylphosphine complexes used in the hydroformylation of olefins is described, which comprises contacting an extracted catalyst liquid containing therein a rhodium-triarylphosphine complex with hydrogen in the presence of an alcohol containing 1 to 8 carbon atoms and water to precipitate a hydrogen-coordinated rhodium-triarylphosphine complex, and recovering the precipitated hydrogen atom-coordinated rhodium-triarylphosphine complex from the liquid.

5 Claims, No Drawings

METHOD FOR THE RECOVERY OF RHODIUM COMPLEXES

FIELD OF THE INVENTION

The present invention relates to a method for the recovery of rhodium complexes. More particularly, it is concerned with a method for the economical and efficient recovery of a rhodium-triarylphosphine complex contained in a catalyst liquid which is extracted or withdrawn from a reaction solution for hydroformylation of olefins (hereinafter this catalyst liquid is referred to as an "extracted catalyst liquid for hydroformylation of olefins") as a modified rhodium-triarylphosphine complex in which a hydrogen atom is coordinated.

BACKGROUND OF THE INVENTION

Rhodium-triarylphosphine complexes are commercially advantageously used as catalysts for the hydroformylation of olefins.

These rhodium-triarylphosphine complexes are chemically very stable in the presence of free triarylphosphine which is present in large excess relative to rhodium. Therefore, they have advantages in that a catalyst liquid can be separated from reaction product by distillation, returned to a reaction zone, and reused, and in that the reaction can be performed continuously while separating the reaction product by distilling away from the reaction zone by gas stripping and allowing the catalyst liquid to remain in the reaction zone. In such hydroformylation reactions of olefins, however, various high boiling by-products are formed and accumulated. In carrying out the reactions continuously, therefore, it is necessary to extract a postion of the catalyst liquid continuously or intermittently from the reaction zone.

The thus-extracted catalyst liquid contains expensive rhodium and, therefore, efficient recovery of rhodium from the extracted catalyst liquid is very important from an economical standpoint. In recovering rhodium from the extracted catalyst liquid, it is desirable to recover it in the form of a complex which is active for the hydroformylation of olefins.

Heretofore known methods of separating and recovering rhodium from the extracted catalyst liquid include a decomposition method using peroxide compounds as described in U.S. Pat. No. 3,547,964 and Japanese Patent Application (OPI) No. 63388/1976 (the term "OPI" as used herein refers to a "published unexamined Japanese patent application"), and a method comprising reducing aldehydes contained in high boiling by-products as described in U.S. Pat. No. 3,560,539.

The decomposition method using peroxide compounds comprises treating the extracted catalyst liquid with an aqueous solution of an acid, such as nitric acid, and a peroxide compound, and after decomposition of excess peroxide compound by heating, treating an aqueous phase resulting from the above treatment with carbon monoxide under pressure in the presence of an organic solvent and a complex-forming substance, such as triphenylphosphine, to obtain the desired rhodium complex in the organic solvent phase.

This decomposition method, however, gives rise to the problem of corrosion of apparatus material since it uses acids. Furthermore, the decomposition method suffers from disadvantages in that since the recovered rhodium complex-containing organic solvent contains sulfate ions ($SO_4^{2-}$) or chloride ions ($Cl^-$), and the sulfur (S) and chlorine (Cl) poison the rhodium complex catalyst, it is necessary to apply a neutralization treatment with an alkali in the reuse of the recovered catalyst to remove the sulfur and chlorine.

In accordance with the method comprising reducing aldehydes in high boiling by-products, the extracted catalyst liquid is brought into contact with (1) alkali metal aluminum hydrides or alkali metal borohydrides, or (2) hydrogen in the presence of a solid hydrogenation catalyst, to reduce 75% of more of the carbonyl groups in the extracted catalyst liquid into hydroxyl groups, thereby modifying the extracted catalyst liquid so that the rhodium complex is sparingly soluble therein, whereby the rhodium complex is crystallized out, and separated and recovered.

This method needs the use of hydride reducing agents as in (1), or the use of hydrogen in the presence of solid hydrogenation catalysts as in (2) for the reduction of carbonyl group-containing compounds in the extracted catalyst liquid into the corresponding alcohols. When the rhodium complex crystallized out by the method is reused for the hydroformylation of olefins, it is necessary to separate the crystallized rhodium complex from the reducing agent in the case of (1) above. Also, in the case of (2) above, it is necessary to separate the crystallized rhodium complex from the solid hydrogenation catalyst, and furthermore, when the catalytic activity of the hydrogenation catalyst is reduced, regeneration treatment of the hydrogenation catalyst is needed. Moreover, the rhodium complex crystallized out by the strong reduction treatment as in (1) and (2) above does not always have enough activity for the hydroformylation of olefins.

As a result of extensive investigations to develop a method of efficiently recovering a rhodium complex from an extracted catalyst liquid for hydroformylation of olefins by a simplified method and, furthermore, as a complex which is active for the hydroformylation reaction, it has been found that when the extracted catalyst liquid for hydroformylation of olefins is brought into contact with hydrogen in the presence of an alcohol containing 1 to 8 carbon atoms and water, modified rhodium-triarylphosphine complexes in which a hydrogen atom is coordinated are precipitated.

SUMMARY OF THE INVENTION

An object of the invention is to provide a method for commercially advantageously separating and recovering a rhodium-triarylphosphine complex contained in an extracted catalyst liquid for hydroformylation of olefins as a modified rhodium-triarylphosphine complex in which a hydrogen atom is coordinated.

Another object of the invention is to provide a method for selectively separating and recovering a rhodium-triarylphosphine complex from an extracted catalyst liquid for hydroformylation of olefins, containing the rhodium-triarylphosphine complex, free triarylphosphine, and high boiling by-products, in the form of a solid complex which has enough activity for the hydroformylation reaction.

The present invention, therefore, provides a method for the recovery of a rhodium complex which comprises bringing an extracted catalyst liquid for hydroformylation of olefins, containing a rhodium-triarylphosphine complex, into contact with hydrogen in the presence of an alcohol containing 1 to 8 carbon atoms and water at a temperature of 95° C. or less to crystallize out a hydrogen atom-coordinated rhodium-triarylphosphine complex, and separating the complex thus-crystallized out from the extracted catalyst liquid.

DETAILED DESCRIPTION OF THE INVENTION

The present invention is directed to a method for the recovery of a rhodium-triarylphosphine complex from an extracted catalyst liquid for hydroformylation of olefins as a hydrogen atom-coordinated rhodium-triarylphosphine complex by selectively coordinating a hydrogen atom to the rhodium-triarylphosphine complex.

Rhodium-triarylphosphine complexes having the triarylphosphine as a ligand can be easily prepared from rhodium compounds, e.g., rhodium hudride, rhodium halide, rhodium carboxylate, rhodium nitrate, and rhodium sulfate, and triarylphosphines by known complex-forming methods. In some cases, the rhodium compound and triarylphosphine can be introduced into a reaction system where they are formed into a complex.

Rhodium compounds which can be used in the preparation of complexes include, for example, hydridocarbonyltris(triphenylphosphine)rhodium, rhodium dicarbonylchloride, rhodium nitrate, rhodium trichloride, rhodium acetate, and rhodium sulfate. Triarylphosphines which can be used in the preparation of complexes include, for example, triphenylphosphine, tri-p-tolylphosphine, tri-m-tolylphosphine, trixylylphosphine, and tris(p-ethylphenyl)phosphine.

The hydroformylation reaction is carried out by reacting an olefin containing 2 to 20 carbon atoms, such as a straight α-olefin, e.g., ethylene, propylene, 1-butene, 1-hexene, and 1-octene, and an olefin having the vinylidene structure, e.g., isobutene, with oxo gas consisting of carbon monoxide and hydrogen ($H_2/CO$ (molar ratio)=$\frac{1}{3}$ to 20/1) in a reaction solvent in the presence of the rhodium-triarylphosphine complex under the conditions of a pressure of 1 to 100 atmospheric pressure and a temperature of 50° to 200° C.

Reaction solvents which can be used in the hydroformylation reaction are those organic solvents which are capable of dissolving the starting materials and catalyst, are inert to the hydroformylation reaction, do not react with the formed aldehyde, and have boiling points higher than that of the formed aldehyde. Examples of such reaction solvents include aromatic hydrocarbons, e.g., benzene, toluene, and xylene, saturated aliphatic hydrocarbons, e.g., heptane and decane, esters, e.g., butyl acetate, and high boiling by-products, e.g., a polycondensate of the formed aldehyde.

The concentration of the rhodium-triarylphosphine complex in the reaction solvent is usually several milligrams per liter to several hundred milligrams per liter as calculated as a rhodium atom. The triarylphosphine as used as a ligand is present in the reaction solvent in an excess amount of several mols to several thousand mols per mol of the rhodium complex in order to increase the stability of the catalyst.

Aldehyde formed by the hydroformylation reaction is separated and recovered from the catalyst liquid by stripping with unreacted gases, distillation or like technique. The catalyst liquid is reused for the reaction either by being allowed to remain in the reaction zone, or by being recycled to the reaction zone. A part of the catalyst liquid is withdrawn continuously or intermittently as an extracted catalyst liquid from the reaction system in order to prevent accumulation of high boiling by-products. In an amount corresponding to the amount withdrawn, a fresh catalyst and fresh triarylphosphine are introduced into the reaction system.

The method of the invention is applied to the extracted catalyst liquid thus-obtained from the reaction system. When the extracted catalyst liquid contains a large amount of reaction solvent which is a good solvent for the hydrogen atom-coordinated rhodium-triarylphosphine complex, it is advantageous to apply the method of the invention after increasing the concentration of the rhodium-triarylphosphine complex in the extracted catalyst liquid usually to 10 mg/l or more, preferably 100 mg/l or more, and most preferably 500 mg/l or more as calculated as a rhodium atom, by removing the solvent from the extracted catalyst liquid by a known method such as distillation, for example, distillation under the conditions of a temperature of 50° to 250° C. and a pressure of 0.5 to 760 mmHg and, furthermore, if desired, by removing a part of the high boiling by-products by the same procedure as above.

In accordance with the method of the invention, the extracted catalyst liquid is brought into contact with hydrogen in the presence of an alcohol containing 1 to 8 carbon atoms and water to precipitate a hydrogen atom-coordinated rhodium-triarylphosphine complex.

Alcohols containing 1 to 8 carbon atoms in the presence of which the extracted catalyst liquid is brought into contact with hydrogen include methyl alcohol, ethyl alcohol, n-propyl alcohol, isopropyl alcohol, n-butyl alcohol, isobutyl alcohol, amyl alcohol, hexyl alcohol, heptyl alcohol, octyl alcohol, ethylene glycol, ethylene glycol monomethyl ether, ethylene glycol monoethyl ether, and glycerin. Preferred examples are alcohols containing 1 to 4 carbon atoms, such as methyl alcohol, ethyl alcohol, n-propyl alcohol, isopropyl alcohol, n-butyl alcohol, isobutyl alcohol, ethylene glycol monomethyl ether, and ethylene glycol monoethyl ether. These alcohols may be used alone or in combination with each other.

The total amount of the alcohol containing 1 to 8 carbon atoms and water being used is usually about 0.1 or more times the weight of the extracted catalyst liquid and preferably about 1 to 50 times. The weight ratio of the water to the alcohol containing 1 to 8 carbon atoms is usually 0.1/99.9 or more and preferably 1/99 to 40/60.

The extracted catalyst liquid is brought into contact with hydrogen under such conditions as to allow for coordination of a hydrogen atom to the rhodium-triarylphosphine complex. The conditions depend on the processing temperature, pressure and time. However, this processing can be performed usually under such conditions that the carbonyl compound in the extracted catalyst liquid is hydrogenated usually to 20% or less and preferably to 10% or less. Most preferably, it is performed under such mild conditions that the carbonyl compound in the extracted catalyst liquid is not substantially hydrogenated. In particular, it is necessary for the processing temperature to be 95° C. or less. When the processing temperature is more than 95° C., the degree of precipitation of the hydrogen atom-coordinated rhodium-triarylphosphine complex is greatly reduced, and the catalytic activity of the complex precipitated is greatly reduced. The processing temperature is preferably 0° to 90° C. and most preferably 0° to 70° C. The processing pressure is, as a hydrogen partial pressure, usually 0.1 kg/cm$^2$G or more and preferably 1 to 100 kg/cm$^2$G. The contact time during which the extracted catalyst liquid is contacted with hydrogen is usually several minutes or more and preferably several minutes to several hours.

After the precipitation of the hydrogen atom-coordinated rhodium-triarylphosphine complex, if the liquid temperature is much lowered, the amount of the complex to be precipitated will be increased.

The hydrogen to be used in the present processing is preferably a high purity hydrogen gas. However, it may contain impurities such as methane and carbon monoxide.

When the extracted catalyst liquid is brought into contact with hydrogen in the presence of an alcohol containing 1 to 8 carbon atoms and water according to the method of the invention, the hydrogen is selectively added to the rhodium-triarylphosphine complex contained in the liquid, resulting in the formation and precipitation of the hydrogen atom-coordinated rhodium-triarylphosphine complex.

On the other hand, when the extracted catalyst liquid is brought into contact with hydrogen in the absence of the alcohol containing 1 to 8 carbon atoms and water, the hydrogen is not substantially incorporated into the rhodium-triarylphosphine complex. Therefore, even if the alcohol containing 1 to 8 carbon atoms and water are added thereto after the above processing, the desired rhodium-triarylphosphine complex is not precipitated at all.

Although the mechanism of the reaction in the method of the invention is not clear, it is assumed that the alcohol containing 1 to 8 carbon atoms and water as used herein serve as poor solvents for the hydrogen atom-coordinated rhodium-triarylphosphine complex and simultaneously, have the effect of accelerating the selective addition of hydrogen for the coordination of the hydrogen atom to the rhodium-triarylphosphine complex.

The hydrogen atom-coordinated rhodium-triarylphosphine complex which is precipitated by the above processing is believed to have the following chemical structure:

$HRhCO(PR_3)_n-(S)$ (wherein $PR_3$ is triarylphosphine, n is an integer of 2 or 3, and S is a solvent). In some cases, the solvent (S) is not contained.

The thus-precipitated hydrogen atom-coordinated rhodium-triarylphosphine complex is subjected to solid-liquid separation by usual solid-liquid separation techniques, such as centrifugal filtration, centrifugal separation, and filtration under pressure, whereby the desired rhodium-triarylphosphine complex is separated and recovered. The hydrogen atom-coordinated rhodium-triarylphosphine complex thus-recovered has enough catalytic activity to perform the hydroformylation, and therefore, as such, it can be recycled to the hydroformylation reaction zone and reused as a hydroformylation catalyst.

Some of the major advantages of the invention are as follows:

(1) A rhodium complex can be efficiently recovered from an extracted catalyst liquid for hydroformylation of olefins by a simplified procedure.

(2) The rhodium complex thus-recovered has enough activity for the hydroformylation reaction, and does not substantially contain impurities which are not desirable for the hydroformylation reaction.

(3) As such, therefore, the recovered rhodium complex can be recycled to the reaction zone for the hydroformylation reaction and reused therein.

Thus, the method of the invention has a very high commercial value.

The following examples are given to illustrate the invention in greater detail although the invention is not limited thereto.

EXAMPLE 1

From an extracted catalyst liquid for the hydroformylation or propylene in which rhodium acetate and triphenylphosphine were used as a rhodium compound and a triarylphosphine, respectively, was removed the reaction solvent by distillation to obtain a still residue liquid having the following composition.

| | |
|---|---|
| Rhodium complex (as calculated as a rhodium atom) | 850 mg/l |
| Triphenylphosphine | 12% by weight |
| Triphenylphosphine oxide | 8% by weight |
| High boiling by-products | 80% by weight |

A mixture of 40 g of the still residue liquid and 240 g of a mixed solvent of ethyl alcohol and water (80/20 by weight) was placed in a 400-ml autoclave equipped with a magnetic stirrer in an inert gas atmosphere, and the autoclave was closed up tight. Then, hydrogen gas was introduced thereinto under pressure at a temperature of 30° C. with moderate stirring until the pressure reached 20 kg/cm²G, and the hydrogen treatment to contact the rhodium complex with hydrogen was performed for 2 hours while maintaining the pressure at that value. At the end of the time, the temperature was lowered to 0° C. and immediately, the hydrogen gas was purged. The mixture was subjected to solid-liquid separation by usual filtration under pressure.

The amount of the thus-recovered rhodium complex was measured, and it was found that a rate of recovery of the rhodium complex was 92% as calculated as a rhodium atom. Gas chromatographic analysis showed that $C_5$ to $C_{15}$ aldehydes remaining in the still residue liquid, such as 2-ethyl hexanal, were not substantially hydrogenated by the hydrogen treatment.

A part of the recovered rhodium complex was washed several times with 50 ml of ethyl alcohol and vacuum-dried at a room temperature. Elemental analysis of the rhodium complex showed that it contained 11% by weight of rhodium and 10% by weight of phosphorus. In an infrared absorption spectrum as determined by the nujol method, there were observed strong bands in the vicinity of 2040 cm$^{-1}$ and 780 cm$^{-1}$, which were believed to result from the Rh-H bond, and a strong band in the vicinity of 1920 cm$^{-1}$ which was believed to result from the Rh-CO bond. Thus, it was found that the infrared absorption spectrum agreed substantially with that of a compound of the formula: $HRhCO[P(C_6H_5)_3]_3$. On the basis of these data, it was believed that the rhodium complex as obtained above was composed mainly of a compound represented by the formula: $HRhCO[P(C_6H_5)_3]_3$.

EXAMPLE 2

The same hydrogen treatment as in Example 1 was performed with the exception that a mixed solvent of isopropyl alcohol and water (80/20 by weight) was used in place of the mixed solvent of ethyl alcohol and water. The rate of recovery of the rhodium complex was 91%, and $C_5$ to $C_{15}$ aldehydes remaining in the still residue liquid, such as 2-ethyl hexanal, were not substantially hydrogenated at all. Infrared analysis showed the same results as for Example 1.

EXAMPLE 3

The same hydrogen treatment as in Example 1 was performed with the exception that a mixed solvent of ethyl alcohol and water (99.82/0.18 by weight) was used in place of the mixed solvent of ethyl alcohol and water (80/20 by weight). The rate of recovery of the rhodium complex was 70%, and $C_5$ to $C_{15}$ aldehydes remaining in the still residue liquid, such as 2-ethyl hexanal, were not substantially hydrogenated at all. Infrared analysis showed the same results as for Example 1.

EXAMPLE 4

The same hydrogen treatment as in Example 1 was performed with the exception that a mixed solvent of ethylene glycol monoethyl ether and water (80/20 by weight) was used in place of the mixed solvent of ethyl alcohol and water. The rate of recovery of the rhodium complex was 71%, and $C_5$ to $C_{15}$ aldehydes remaining in the still residue liquid, such as 2-ethyl hexanal, were not substantially hydrogenated at all. Infrared analysis showed the same results as for Example 1.

EXAMPLE 5

The same hydrogen treatment as in Example 1 was performed with the exception that the treatment temperature was changed to 60° C. The rate of recovery of the rhodium complex was 90%, and $C_5$ to $C_{15}$ aldehydes remaining in the still residue liquid, such as 2-ethyl hexanal, were not substantially hydrogenated at all. Infrared analysis showed the same results as for Example 1.

EXAMPLE 6

The same hydrogen treatment as in Example 1 was performed with the exception that 384 g of the mixed solvent was used in place of 240 g of the mixed solvent and that the treatment temperature was changed to 80° C. The rate of recovery of the rhodium complex was 68%, and $C_5$ to $C_{15}$ aldehydes remaining in the still residue liquid, such as 2-ethyl hexanal, were not substantially hydrogenated at all. Infrared analysis showed the same results as for Example 1.

EXAMPLE 7

The same hydrogen treatment as in Example 1 was performed with the exception that a mixed solvent of methyl alcohol and water (83/17 by weight) was used in place of the mixed solvent of ethyl alcohol and water. The rate of recovery of the rhodium complex was 65%, and $C_5$ to $C_{15}$ aldehydes remaining in the still residue liquid, such as 2-ethyl hexanal, were not substantially hydrogenated at all. Infrared analysis showed the same results as for Example 1.

EXAMPLE 8

The same hydrogen treatment as in Example 1 was performed with the exception that a mixed solvent of n-propyl alcohol and water (85/17 by weight) was used in place of the mixed solvent of ethyl alcohol and water. The rate of recovery of the rhodium complex was 63%, and $C_5$ to $C_{15}$ aldehydes remaining in the still residue liquid, such as 2-ethyl hexanal, were not substantially hydrogenated at all. Infrared analysis showed the same results as for Example 1.

COMPARATIVE EXAMPLE 1

The same hydrogen treatment as in Example 1 was performed with the exception that the treatment temperature was changed to 100° C. The rate of recovery of the rhodium complex was only 10%.

REFERENCE EXAMPLE 1

In this example, the activity of the recovered rhodium complexes for the hydroformylation of olefin was tested.

Each of the rhodium complexes (not yet washed with ethyl alcohol) recovered in Examples 1 and 3, and Comparative Example 1 was dissolved in a toluene solution containing 10% by weight of triphenylphosphine in an amount (as calculated as a rhodium atom) of 100 mg/l to prepare a catalyst solution. Using the thus-prepared catalyst solution, the hydroformylation of propylene was performed. The conversion of propylene, the apparent rate constant, and the selectivity of butyraldehyde were determined for each hydroformylation reaction.

For comparison, the hydroformylation of propylene was performed under the same conditions as above by the use of hydridocarbonyltris(triphenylphosphine)rhodium which had been prepared from rhodium trichloride ($RhCl_3.3H_2O$) by a conventional procedure.

The hydroformylation reaction was carried out as follows:

A 200-ml autoclave equipped with a magnetic stirrer was charged with 50 ml of the catalyst solution and 10 g of propylene. A mixed gas of hydrogen and carbon monoxide (oxo gas: $H_2/CO=1/1$ by mol) was introduced into the autoclave under pressure at a temperature of 120° C., and the reaction was started while maintaining the reaction pressure at 50 kg/cm$^2$G. In order to maintain the pressure at that value during the reaction, the autoclave was connected to a high pressure oxo gas holder through a pressure controller and a fresh oxo gas was supplied thereinto in an amount corresponding to the amount of the oxo gas consumed. After three hours, the autoclave was quenched, and the residual propylene and formed butyraldehyde in gas and liquid phases were determined by gas chromatography. The apparent first-order rate constant was determined by the curve of reduction in the oxo gas pressure in the high pressure gas holder.

The results are shown in Table 1.

TABLE 1

|  | Rhodium Complex Recovered in Example 1 | Rhodium Complex Recovered in Example 3 | Rhodium Complex Recovered in Comparative Example 1 | Rhodium Complex Prepared from Rhodium Trichloride |
|---|---|---|---|---|
| Conversion of Propylene (%) | 99 or more | 99 or more | 99 or more | 99 or more |
| Selectivity of | 99 | 99 | 99 | 99 |

TABLE 1-continued

|  | Rhodium Complex Recovered in Example 1 | Rhodium Complex Recovered in Example 3 | Rhodium Complex Recovered in Comparative Example 1 | Rhodium Complex Prepared from Rhodium Trichloride |
| --- | --- | --- | --- | --- |
| Butyraldehyde Apparent Rate Constant (first-order) (l/hr) | 6.2 | 6.2 | 3.0 | 6.2 |

It can be seen from the results shown in Table 1 that the rhodium complex recovered by the method of the invention has enough activity for the hydroformylation of olefins, does not substantially contain impurities which are harmful for the hydroformylation reaction, and therefore, can be reused, as such, in the hydroformylation reaction with the desired conversion and selectivity, and rate of reaction.

While the invention has been described in detail and with reference to specific embodiments thereof, it will be apparent to one skilled in the art that various changes and modifications can be made therein without departing from the spirit and scope thereof.

What is claimed is:

1. A method for the recovery of rhodium complex from a catalyst liquid containing a rhodium complex and used in the hydroformylation of an olefin, said liquid containing a rhodium complex containing therein triarylphosphine as a ligand, which consists essentially of contacting said liquid with hydrogen in the presence of an added alcohol containing 1 to 8 carbon atoms and water in a weight ratio of water to alcohol of 0.1:99.9 or more at a temperature of 95° C. or less and under the conditions such that carbonyl compounds in said liquid are hydrogenated to 20% or less to precipitate a hydrogen atom-coordinated rhodium-triarylphosphine complex, and separating the precipitated rhodium-triarylphosphine complex from the liquid.

2. The method as claimed in claim 1, wherein the triarylphosphine is triphenylphosphine.

3. The method as claimed in claim 1 or 2, wherein the alcohol containing 1 to 8 carbon atoms is an alcohol containing 1 to 4 carbon atoms.

4. The method as claimed in claim 1 or 2 wherein the extracted catalyst liquid is contacted with hydrogen at a temperature of 0° to 90° C.

5. The method as claimed in claim 3, wherein the extracted catalyst liquid is contacted with hydrogen at a temperature of 0° to 90° C.

* * * * *